United States Patent
Fujinami et al.

(10) Patent No.: US 8,236,980 B2
(45) Date of Patent: Aug. 7, 2012

(54) LITHIUM SALT

(75) Inventors: Tatsuo Fujinami, Hamamatsu (JP); Ruoyuan Tao, Hamamatsu (JP); Masaki Matsui, Susono (JP)

(73) Assignees: National University Corporation Shizuoka University, Shizuoka-Ken (JP); Toyota Jidosha Kabushiki Kaisha, Aichi-ken (JP)

( * ) Notice: Subject to any disclaimer, the term of this patent is extended or adjusted under 35 U.S.C. 154(b) by 623 days.

(21) Appl. No.: 12/377,716

(22) PCT Filed: Sep. 13, 2007

(86) PCT No.: PCT/JP2007/067862
§ 371 (c)(1),
(2), (4) Date: Sep. 23, 2009

(87) PCT Pub. No.: WO2008/032793
PCT Pub. Date: Mar. 20, 2008

(65) Prior Publication Data
US 2010/0010249 A1 Jan. 14, 2010

(51) Int. Cl.
*C07F 7/00* (2006.01)
*C07F 9/00* (2006.01)
(52) U.S. Cl. ............... 556/76; 556/81; 556/446; 568/6; 568/15
(58) Field of Classification Search ............ 556/76, 556/81, 446; 568/6, 15
See application file for complete search history.

(56) References Cited

U.S. PATENT DOCUMENTS

| 4,914,161 | A | 4/1990 | Muller et al. |
|---|---|---|---|
| 2002/0001755 | A1 | 1/2002 | Heider et al. |
| 2006/0068295 | A1 | 3/2006 | Xu et al. |

FOREIGN PATENT DOCUMENTS

| JP | 62-64073 | 3/1987 |
|---|---|---|
| JP | 2001-354681 | 12/2001 |
| JP | 2003-146941 | 5/2003 |
| JP | 2004-67554 | 3/2004 |
| JP | 2004-307481 | 11/2004 |
| JP | 2005-126339 | 5/2005 |
| JP | 2005-229103 | 8/2005 |
| JP | 2005-251511 | 9/2005 |

OTHER PUBLICATIONS

Supplementary European Search Report for EP Appl. No. 07 80 7269 mailed Oct. 18, 2010.
Mudryk, B. et al., "Synthetically Useful Dianions via Reductive Lithiation of Tetrahydrofurans by Aromatic Radical Anions," Jounal of the American Chemical Society, vol. 113, No. 5, (1991), pp. 1866-1867.

*Primary Examiner* — Porfirio Nazario Gonzalez
(74) *Attorney, Agent, or Firm* — Finnegan, Henderson, Farabow, Garrett & Dunner, LLP (57) ABSTRACT

The principal object of the invention is to provide a lithium salt having excellent ion conductivity. The invention solves the problem by providing a lithium salt having a structure represented by the general formula (1): in which "M" represents B, Si, Ge, P, As or Sb; "X" represents the valence of "M"; "$R_1$" represents —$C_mH_{2m}$— whereupon "m" is an integer of 1 to 4; "$R_2$" represents —$C_kH_{2k+1}$ whereupon "k" is an integer of 1 to 8; and "n" represents 0 to 12.

6 Claims, 5 Drawing Sheets

LITHIUM SALT

CROSS-REFERENCE TO RELATED APPLICATIONS

This application is a national phase application of International Application No. PCT/JP2007/067862, filed Sep. 13, 2007, and claims the priority of Japanese Application No. 2006-248539, filed Sep. 13, 2006, the contents of both of which are incorporated herein by reference.

TECHNICAL FIELD

The present invention relates to a lithium salt which can give a lithium ionic liquid with low viscosity and high ion conductivity.

BACKGROUND ART

Lithium salts which have conventionally been used in electrolytes etc. in lithium secondary batteries are solids having a highly dissociative chemical structure and do not show ion conductivity by themselves. Accordingly, the lithium salts have conventionally been used after dissolution in a suitable solvent in order to confer ion conductivity thereon.

Solvents used in dissolving lithium salts are generally non-aqueous solvents from the viewpoint of suppressing a reaction with an electrode active material. General non-aqueous solvents are combustible, and thus use of such non-aqueous solvents is preferably avoided in lithium secondary batteries widely usable for consumer application.

For withholding the use of non-aqueous solvents, a lithium ionic liquid having lithium ion conductivity and high dissociation property (self-dissociation property) by the lithium salt itself has been proposed. For example, Patent Document 1 discloses a lithium ionic liquid having a lithium cation and a quaternary anion having the XIII group element (B, Al, Ga, In, Ti) as the central element. However, there is the case where the lithium ionic liquid disclosed in Patent Document 1 cannot attain sufficiently excellent ion conductivity.

Patent Document 2 discloses a lithium ionic liquid represented by $LiAlX_n(OY)_{4-n}$ wherein "X" is an electron-withdrawing substituent and "Y" is an oligoether group. However, the dissociation property of the lithium ionic liquid disclosed in Patent Document 2 is not high, and depending on the type of the electron-withdrawing group "X", its viscosity may increase, and as a result, oligoether groups involved in conduction of lithium cations are hardly contacted with one another, thus failing to attain sufficiently excellent ion conductivity in some cases.

Patent Document 3 discloses a non-aqueous electrolyte for electrochemical element including a fluorine compound and an ambient temperature molten salt consisting of an onium cation and a non-aluminate anion. The addition of $LiBF_3(CF_3)$, $LiBF_3(C_2F_5)$ and $LiBF_3(C_3F_7)$ etc., as lithium salts is also disclosed. However, the non-aqueous electrolyte for electrochemical element disclosed in Patent Document 3 includes various ions to make the system complex so that the movement of lithium cations may be inhibited.

Patent Document 1: Japanese Patent Application Laid-Open (JP-A) No. 2004-307481
Patent Document 2: JP-A No. 2003-146941
Patent Document 3: JP-A No. 2005-229103

DISCLOSURE OF INVENTION

Problem to be Solved by the Invention

The present invention has been completed in view of the problem described above, and the principal object of the present invention is to provide a lithium salt excellent in ion conductivity. Particularly, the present invention provides a lithium salt which can give a lithium ionic liquid with high dissociation property, low viscosity and high ion conductivity.

Means for Solving Problem

To solve the problem, the present invention provides a lithium salt having a structure represented by the general formula (1).

[Chemical Formula 1]

General Formula (1)

In the above-mentioned general formula (1), "M" represents B, Si, Ge, P, As or Sb; "X" represents the valence of "M"; "$R_1$" represents —$C_mH_{2m}$— whereupon "m" is an integer of 1 to 4; "$R_2$" represents —$C_kH_{2k+1}$ whereupon "k" is an integer of 1 to 8; and "n" represents 0 to 12.

According to the present invention, the atoms bound to the central atom (M) of the anion moiety are an ether chain and F only, and thus the molecular weight of the anion moiety can be decreased. Accordingly, when the lithium salt of the present invention is a lithium ionic liquid for example, the liquid can have low viscosity and high ion conductivity.

In the present invention, it is preferable that $M^-F_x$ is $B^-F_3$ in the general formula (1). This is because a lithium salt with high ion conductivity can be obtained.

In the present invention, it is preferable that $M^-F_x$ is $B^-F_3$, "$R_1$" is —$C_2H_4$—, and $R_2$ is —$CH_3$ in the general formula (1). Thereby, a lithium salt with high conductivity can be obtained.

The present invention provides a method for producing a lithium salt, which comprises carrying out the following reaction formulae (1) and (2).

[Chemical Formula 2]

(Reaction Formula 1)

(Reaction Formula 2)

n the above-mentioned reaction formulae (1) and (2), "p" represents an integer of 1 to 4; "$R_1$" represents —$C_mH_{2m}$— whereupon "m" is an integer of 1 to 4; "$R_2$" represents —$C_kH_{2k+1}$ whereupon "k" is an integer of 1 to 8; "n" represents 0 to 12; "M" represents B, Si, Ge, P, As or Sb; and "X" represents the valence of "M".

The present invention has an advantage that a lithium salt can be easily obtained by using an alkyl lithium and an $MF_x$ compound.

Effect of the Invention

In the present invention, there is brought about an effect of obtaining a lithium salt excellent in ion conductivity.

BEST MODE FOR CARRYING OUT THE INVENTION

Hereinafter, the lithium salt and the method for producing a lithium salt of the present invention are described in detail.

A. Lithium Salt

First, the lithium salt of the present invention is described. The lithium salt of the present invention is characterized by having a structure represented by the general formula (1) above.

According to the present invention, the atoms bound to the central atom (M) of the anion moiety are an ether chain and F only, and thus the molecular weight of the anion moiety can be decreased. Accordingly, when the lithium salt of the present invention is a lithium ionic liquid for example, the liquid can have low viscosity and high ion conductivity. Lithium cations are conductive usually through an ether chain, and lithium ions are estimated to diffuse easily with decreasing viscosity to increase ion conductivity. Although the conventional lithium salts have a property of easily solidifying and hardly liquefying with a decreasing molecular weight, a lithium ionic liquid stable with a relatively low molecular weight can be obtained in the present invention.

Conventionally, a lithium ionic liquid wherein an electron-withdrawing substituent is bound to an atom bound to the central atom (M) in the anion portion thereof is known, but the electron-withdrawing substituent of such lithium ionic liquid has a large molecular weight, thus increasing the viscosity of the lithium ionic liquid, resulting in failure to demonstrate sufficient ion conductivity in some cases. The lithium salt of the present invention, on the other hand, has a structure wherein the central atom (M) in the anion portion binds to fluorine atoms besides an ether chain represented by $—O(R_1O)_nR_2$. Accordingly, a lithium ionic liquid having a low molecular weight, low viscosity and high ion conductivity can be obtained. The lithium salt of the present invention is useful for example as an electrolyte for lithium secondary battery.

Hereinafter, each constitution of the lithium salt of the present invention is described.

In the general formula (1), "M" represents B (boron), Si (silicon), Ge (germanium), P (phosphorus), As (arsenic) or Sb (antimony). Particularly, in the present invention, "M" is preferably B, Si or P, and particularly preferably B. In the general formula (1), "X" represents the valence of "M" and indicates the number of F (fluorine), which depending on the type of "M", bound to "M". Specifically, $M^-F_x$ in the general formula (1) represents $B^-F_3$, $Si^-F_4$, $Ge^-F_4$, $P^-F_5$, $As^-F_5$ or $Sb^-F_5$. In the present invention, $M^-F_x$ is particularly preferably $B^-F_3$.

In the general formula (1), "$R_1$" represents $—C_mH_{2m}—$ wherein "m" is an integer of 1 to 4. It is preferable that "m" is an integer in the range of 2 to 3, and particularly preferably to be 2. That is to say, in the present invention, "$R_1$" is particularly preferably $—C_2H_4—$. In the general formula (1), "$R_2$" represents $—C_kH_{2k+1}$ wherein "k" is an integer of 1 to 8. Furthermore, "k" is preferably an integer in the range of 1 to 3, and particularly preferably to be 1. That is to say, in the present invention, "$R_2$" is particularly preferably $—CH_3$.

In the general formula (1), "n" represents 0 to 12. Particularly, in the present invention, "n" is preferably a numerical value at which the lithium salt of the present invention can be converted into a lithium ionic liquid. Such a numerical value differs significantly depending on the constitution of the lithium salt of the present invention, and for example, "n" is preferably in the range of 3 to 12.

The nature of the lithium salt of the present invention varies significantly depending on properties such as the molecular weight of $—(R_1O)_nR_2$ in the general formula (1). Specifically, when the molecular weight of $—(R_1O)_nR_2$ is increased, the nature of $—(R_1O)_nR_2$ in the lithium salt is dominating, and thus the lithium salt changes from solid to liquid. From the viewpoint of ion conductivity, the lithium salt of the present invention is preferably a lithium ionic liquid. The molecular weight of $—(R_1O)_nR_2$ is preferably in the range of 150 to 540 for example. This is because when the molecular weight is less than the above range, the lithium salt may not form a lithium ionic liquid, while when the molecular weight is higher than the above range, the viscosity of the lithium salt may increase to reduce ion conductivity.

Particularly, in the present invention, $—(R_1O)_nR_2$ is preferably $—(C_2H_4O)_nCH_3$. In this case, "n" represents 0 to 12 as described above and is preferably in the range of 1 to 12, more preferably in the range of 3 to 12, even more preferably 5 to 9. This is because, when "n" is 1 or more, ion conductivity can be improved; when "n" is 3 or more, the lithium salt of the present invention can form a lithium ionic liquid; and further, when "n" is in the range of 5 to 9, a lithium ionic liquid having suitable viscosity can be obtained. When the lithium salt wherein $—(R_1O)_nR_2$ is $—(C_2H_4O)_nCH_3$ is to be obtained, $CH_3(OC_2H_4)_nOH$ (polyethylene glycol monomethyl ether) described later may be used as a raw material, and in this case, "n" means the average polymerization degree of the ethylene oxide group.

The ratio (O/Li) of the number of oxygen atoms to the number of lithium atoms, derived from $(R_1O)_nR_2$, is not particularly limited, and is for example preferably in the range of 2/1 to 90/1, still more preferably in the range of 6/1 to 30/1, and even more preferably 10/1 to 18/1.

The lithium salt of the present invention may be either solid or liquid, but is preferably liquid from the viewpoint of ion conductivity. When the lithium salt of the present invention is solid, it can be dissolved in a suitable solvent to form a liquid electrolyte. The solvent is not particularly limited as long as it can dissolve the lithium salt of the present invention. Examples of the solvent include ethylene carbonate, propylene carbonate, diethyl carbonate, dimethyl carbonate, γ-butyrolactone, diethylene glycol dimethyl ether, and ethylene glycol dimethyl ether. These solvents may be used singly or as a mixed solvent of two or more thereof.

A method for producing the lithium ion represented by the general formula (1) is not particularly limited, and specifically the method described in "B. Method for Producing Lithium Salt" can be mentioned.

B. Method for Producing Lithium Salt

Next, the method for producing a lithium salt of the present invention is described. The method for producing a lithium salt of the present invention comprises carrying out the following reaction formulae (1) and (2), thereby yielding the lithium salt.

[Chemical Formula 3]

(Reaction Formula 1)

(Reaction Formula 2)

In the above-mentioned reaction formulae (1) and (2), "p" represents an integer of 1 to 4, "$R_1$" represents $—C_mH_{2m}—$ whereupon "m" is an integer of 1 to 4; "$R_2$" represents $—C_kH_{2k+1}$ whereupon "k" is an integer of 1 to 8; "n" represents 0 to 12; "M" represents B, Si, Ge, P, As or Sb; and "X" represents the valence of "M".

The present invention has an advantage that a lithium salt can be obtained by using an alkyl lithium and an $MF_x$ compound. In the conventional method for producing lithium salts, $LiBH_4$, $LiAlH_4$ etc. have been generally used as the starting materials, but these reagents easily react with water and thus have the problem of difficult handling and poor workability during production of the lithium salt. In the method for producing the lithium salt according to the present invention, on the other hand, the lithium salt can be obtained under relatively moderate conditions by using an alkyl lithium such as butyl lithium and an $MF_x$ compound such as $BF_3$ gas or $BF_3$ complex.

Next, the method for producing the lithium salt of the present invention is described by reference to the respective reactions.

1. Reaction Formula (1)

In the reaction formula (1), $LiC_pH_{2P+1}$ represents an alkyl lithium. This compound serves as a lithium source for the lithium salt obtained by the present invention. What "p" represents is an integer of 1 to 4, any of which may be similarly used to yield the objective compound, but "p" is preferably 4 which is an integer in the most common alkyl lithium. That is, $LiC_pH_{2P+1}$ is preferably normal butyl lithium (n-LiBu).

In the reaction formula (1), $R_2(OR_1)_nOH$ is an OH derivative of the group represented by $—(R_1O)_nR_2$ in the general formula (1). A description of "$R_1$", "$R_2$" and "n" in $R_2(OR_1)_n$OH is omitted because they are the same as described above in "A. Lithium Salt". In the present invention, $R_2(OR_1)_nOH$ is preferably $CH_3(OCH_2CH_2)_nOH$.

Although the amounts of $LiC_pH_{2P+1}$ and $R_2(OR_1)_nOH$ used are not particularly limited, the molar ratio thereof is usually $LiC_pH_{2P+1}:R_2(OR_1)_nOH=1:1$.

In the reaction formula (1), $LiC_pH_{2P+1}$ and $R_2(OR_1)_nOH$ described above are dissolved and reacted in a suitable solvent. Such solvent is not particularly limited as long as it can dissolve the above compounds and does not react with $LiC_pH_{2P+1}$. Examples of such solvent include tetrahydrofuran (THF), and dioxane. Although the reaction temperature in the reaction formula (1) is not particularly limited as long as side reactions can be inhibited, the reaction temperature is usually 0° C. or less, more preferably −20° C. or less.

By the reaction represented by the reaction formula (1), $R_2(OR_1)_nOLi$ can be obtained. By the reaction represented by the reaction formula (1), $C_pH_{2p+2}$ gas is usually generated. For example, when $LiC_4H_8$ is used, $C_4H_9$ gas is generated according to the reaction formula (1). Generation of $C_4H_9$ gas can be confirmed by gas chromatography (GC).

2. Reaction Formula (2)

In the reaction formula (2), $R_2(OR_1)_nOLi$ is obtained by the reaction represented by the reaction formula (1). The $MF_x$ compound is a compound giving the $M^-F_x$ moiety in the general formula (1). A description of "M" is omitted because it is the same as described above in "A. Lithium Salt". The $MF_x$ compound refers specifically to a $BF_3$ compound, an $SiF_4$ compound, a $GeF_4$ compound, a $PF_5$ compound, an $AsF_5$ compound or an $SbF_5$ compound.

The $BF_3$ compound, although not particularly limited as long as it gives a lithium salt represented by the general formula (1), includes for example $BF_3$ and a $BF_3$ complex. Because $BF_3$ is gaseous at ordinary temperature and pressure, the reaction represented by the reaction formula (2) can be carried out by blowing $BF_3$ gas into the reaction solution. On the other hand, the $BF_3$ complex, although not particularly limited as long as it is a complex having an unshared electron pair coordinated and bonded with boron of $BF_3$, includes for example $BF_3Et_2O$, $BF_3Me_2O$, $BF_3$-THF, etc. Among them, $BF3Et_2O$ is preferable. Because the $BF_3$ complex is usually liquid, the reaction represented by the reaction formula (2) can be carried out by adding a solution including the $BF_3$ complex.

Although the amounts of $R_2(OR_1)_nOLi$ and $MF_x$ compound used are not particularly limited, the molar ratio thereof is usually in the range of $R_2(OR_1)_nOLi:MF_x$ compound=1:1 to 1:2.

In the reaction formula (2), $R_2(OR_1)_nOLi$ and the $MF_x$ compound are dissolved and reacted in a suitable solvent. Such solvent is not particularly limited as long as it can dissolve the above compounds. A description of the solvent is omitted because its specific examples are the same as used in the reaction formula (1). Although the reaction temperature in the reaction formula (2) is not particularly limited as long as side reactions can be inhibited, a description of the reaction temperature is omitted because the temperature is the same as used in the reaction formula (1).

In the present invention, it is preferable that the reactions represented by the reaction formulae (1) and (2) are successively conducted. That is, it is preferable that $LiC_pH_{2P+1}$ is reacted with $R_2(OR_1)_nOH$ (reaction formula (1)) and then the $MF_x$ compound is added to and reacted with the reaction solution (reaction formula (2)). By removing the solvent etc. from the resulting reaction solution, $LiMF_xO(R_1O)_nR_2$ represented by the general formula (1) is obtained.

The present invention is not limited to the embodiments described above. The embodiments described above are mere illustrative, and those having substantially the same constitution and the same working effect as in the technical idea described in the claims of the present invention are included in the technical scope of the present invention.

EXAMPLES

Hereinafter, the present invention is described in more detail by reference to the Examples.

Example 1

A lithium salt was prepared according to the following reaction formulae (i) and (ii):

[Chemical Formula 4]

(Reaction Formula i)

(Reaction Formula ii)

A solution of 7.2 mmol n-butyl lithium (n-BuLi) dissolved in 10 mL tetrahydrofuran (THF), a solution of 7.2 mmol polyethylene glycol monomethyl ether (PEGMME, average molecular weight 350, average polymerization degree 7.2) dissolved in 10 mL THF, and a solution of 7.2 mmol $BF_3Et_2O$ dissolved in 10 mL tetrahydrofuran (THF), were added in this order to a reaction container cooled at about −20° C. in an acetone bath and mixed with each other to yield a yellow liquid. Then, the reaction solution was returned gradually to room temperature and stirred overnight. Thereafter, the solvent was distilled away, and the reaction mixture was dried at 30° C. for 24 hours under reduced pressure to give a brown viscous liquid. A lithium metal piece was introduced into it and stirred for one day at room temperature, and then a trace amount of impurities reacting with the lithium metal were removed, whereby a brown viscous liquid (lithium ionic liquid) was obtained.

Figure 1:
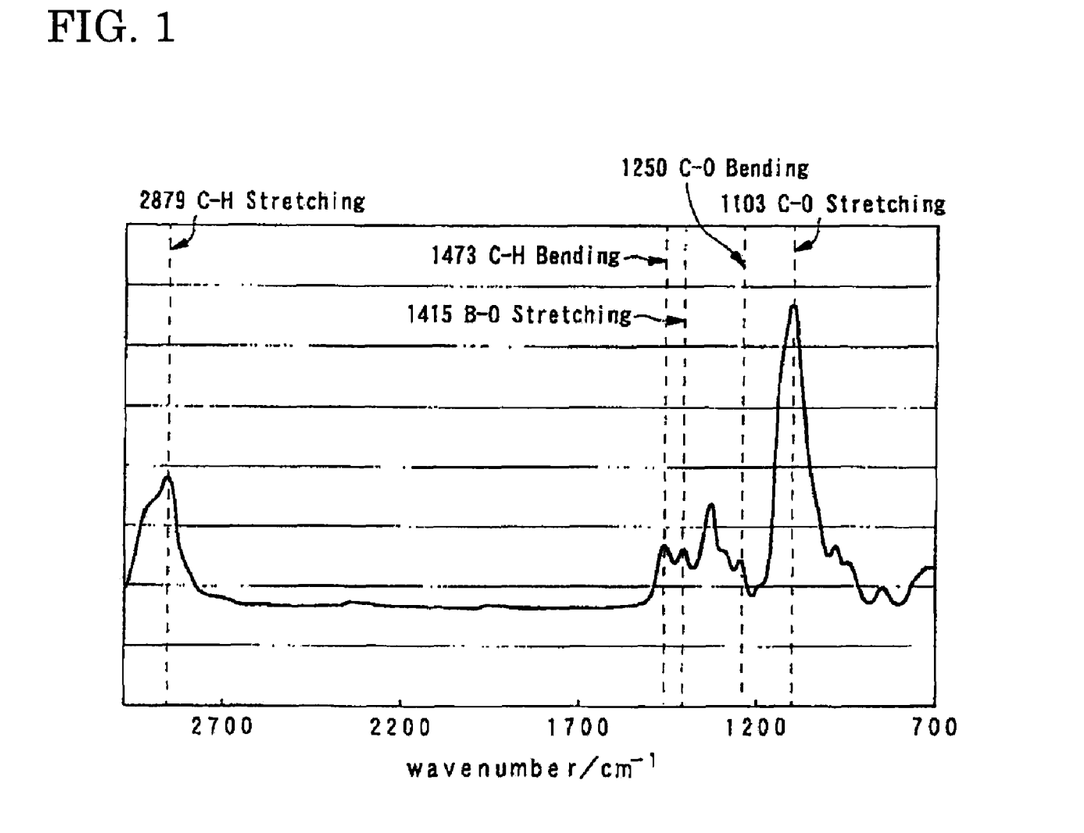
FIG. 1 is a graph showing an IR spectrum of the lithium ionic liquid obtained in Example 1.
Figure 2:
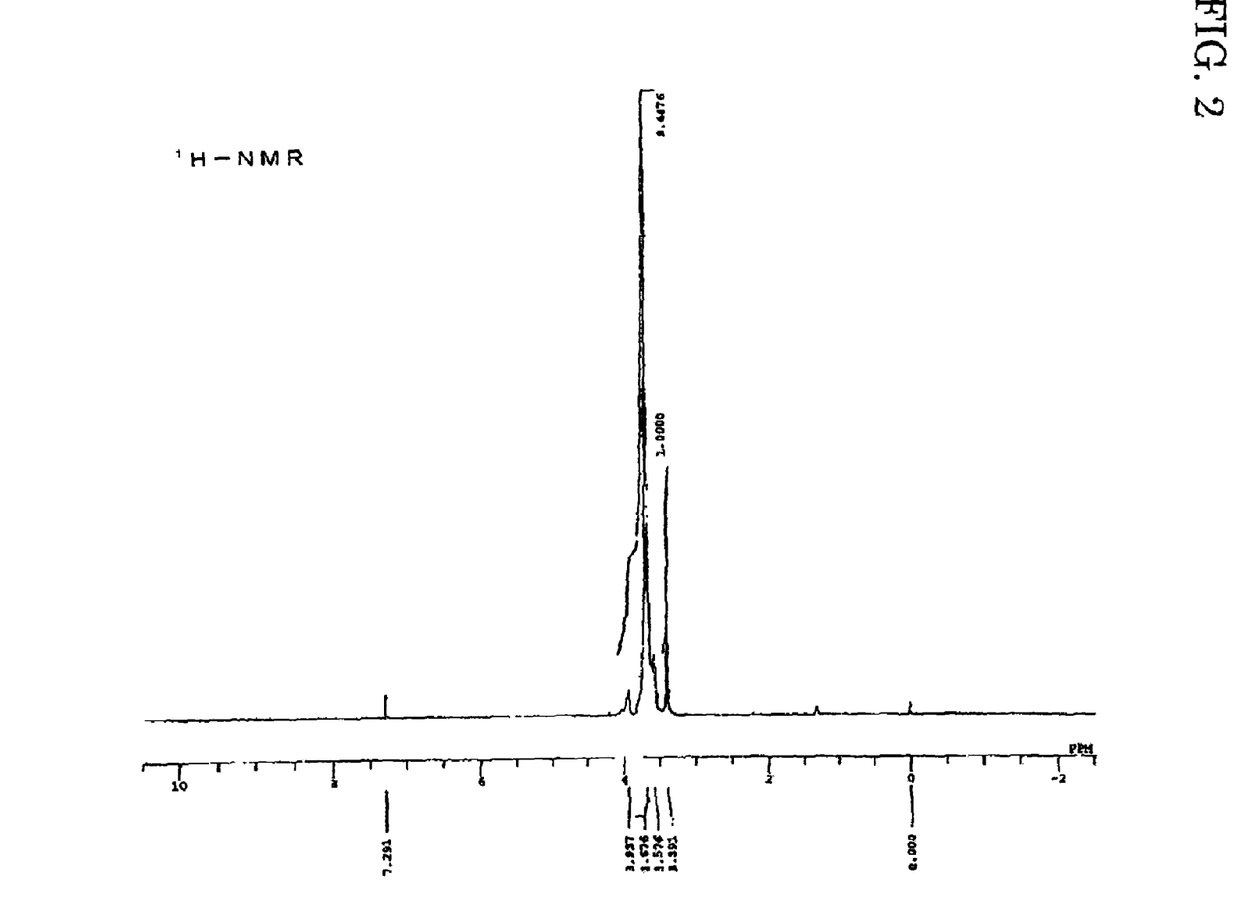
FIG. 2 is a graph showing a $^1$H-NMR spectrum of the lithium ionic liquid obtained in Example 1.
Figure 3:
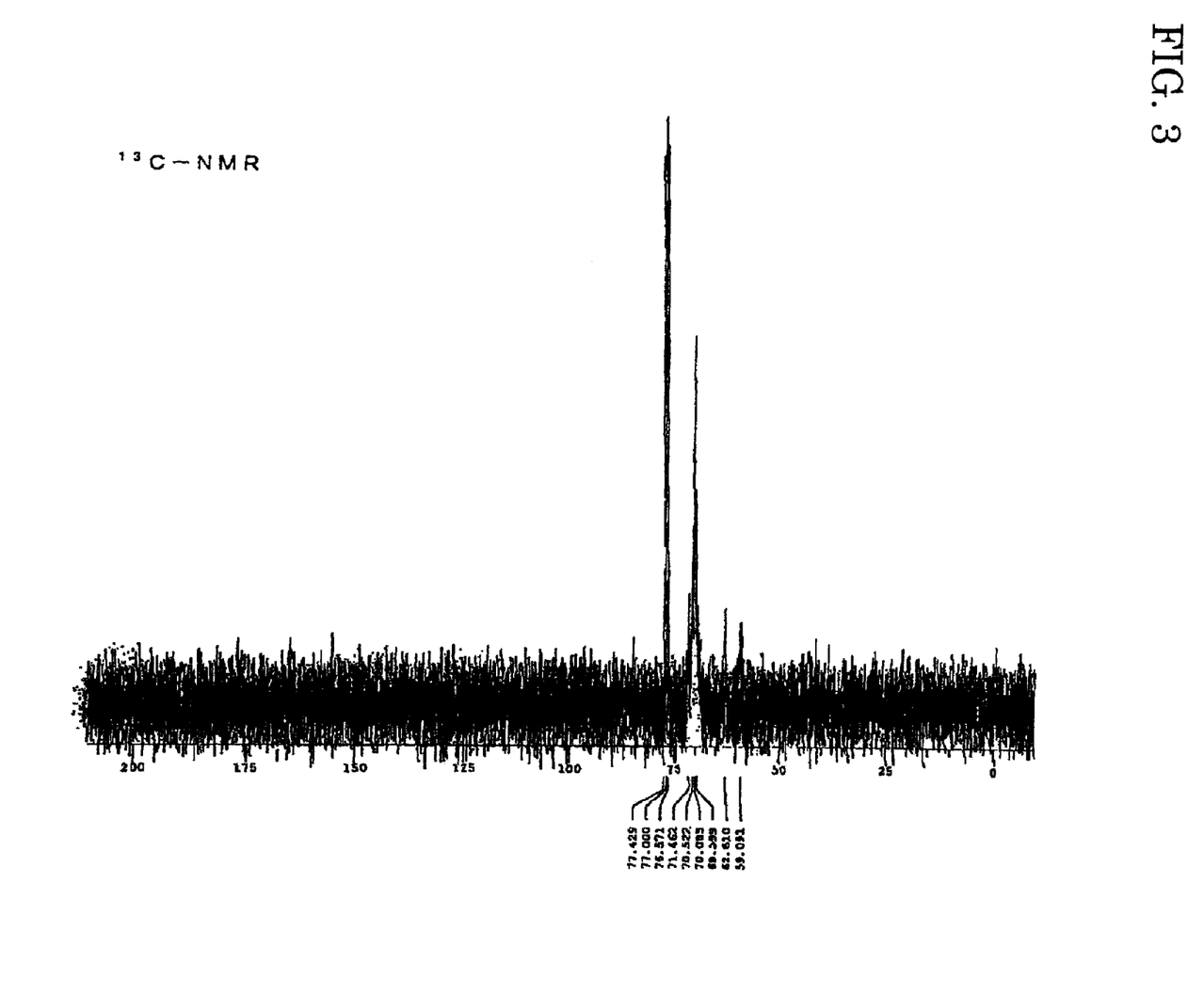
FIG. 3 is a graph showing a $^{13}$C-NMR spectrum of the lithium ionic liquid obtained in Example 1.

When an infrared absorption spectrum (IR spectrum) and nuclear magnetic resonance spectrum (NMR spectrum) of the resulting lithium ionic liquid were measured, it was confirmed that the objective product had been synthesized. The result of the IR spectrum is shown in FIG. 1, the result of the $^1$H-NMR spectrum is shown in FIG. 2, and the result of the $^{13}$C-NMR spectrum is shown in FIG. 3. From the result of IR spectrum, a B—O bond could be confirmed, and it was suggested that the objective product had been synthesized. From the result of $^1$H-NMR spectrum and $^{13}$C-NMR spectra, it was suggested that the objective product had been synthesized.

Example 2

A lithium ionic liquid was obtained in the same manner as in Example 1 except that PEGMME having an average polymerization degree of 3 was used in place of the PEGMME having an average polymerization degree of 7.2. When the obtained IR spectrum, $^1$H-NMR spectrum and $^{13}$C-NMR spectrum were measured, it was suggested that the objective product had been synthesized.

Example 3

A lithium ionic liquid was obtained in the same manner as in Example 1 except that PEGMME having an average polymerization degree of 11.8 was used in place of the PEGMME having an average polymerization degree of 7.2. When the obtained IR spectrum, $^1$H-NMR spectrum and $^{13}$C-NMR spectrum were measured, it was suggested that the objective product had been synthesized.

Evaluation (1) Measurement of Ion Conductivity

The electrolyte was injected into between 2 stainless metal blocking electrodes and measured for its alternating-current impedance at 0 to 80° C. with a frequency response analyzer (FRA, trade name: Solartron 1260, manufactured by Solartron), to measure the ion conductivity of the electrolyte.

Figure 4:
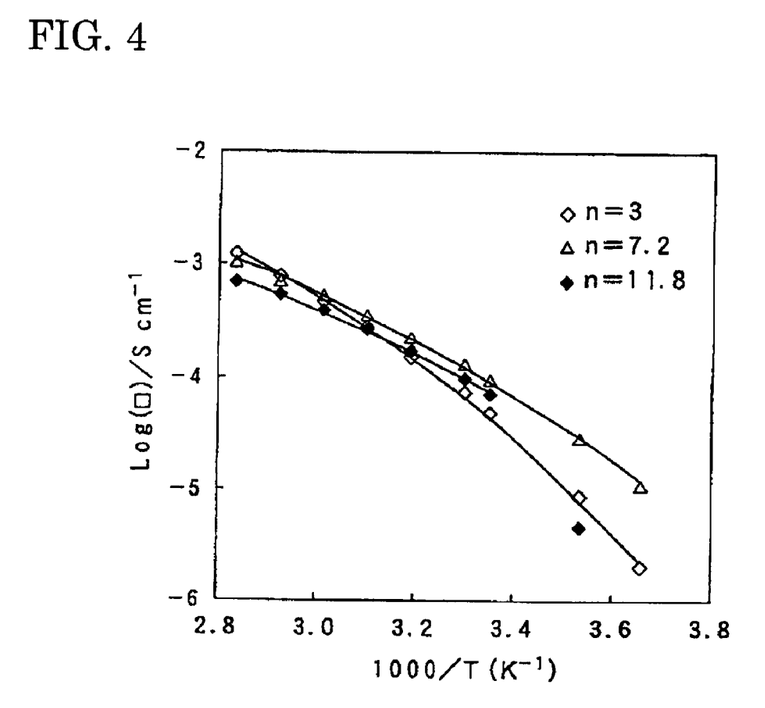
FIG. 4 is a graph showing the results of ion conductivity measurement of the lithium ionic liquids obtained in Examples 1 to 3.

FIG. 4 is a graph showing the results of ion conductivity measurement of the lithium ionic liquids obtained in Examples 1 to 3. The solid line in the figure is obtained by subjecting the experimental data to a nonlinear least-squares method by a VTF equation. As shown in FIG. 4, the lithium ionic liquids obtained in Examples 1 to 3 were revealed to show excellent ion conductivity.

(2) Cyclic Voltammetry Measurement

Cyclic voltammetry measurement (CV measurement) of the electrolyte was carried out at 50° C. by using Solartron 1260 (potentiostat/galvanostat, manufactured by Solartron) and a 3-electrode cell (counter electrode and reference electrode: lithium foils, working electrode: stainless steel (surface area 0.01 cm$^2$)).

Figure 5:
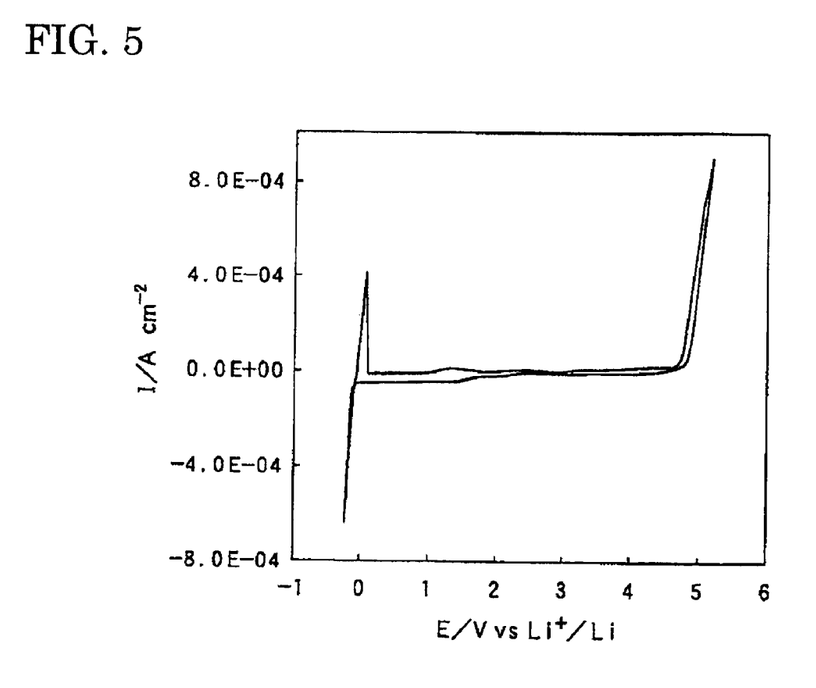
FIG. 5 is a graph showing the result of CV measurement of the lithium ionic liquid obtained in Example 1.

FIG. 5 is a graph showing the result of CV measurement of the lithium ionic liquid obtained in Example 1. The sweep velocity was 2 mV/s. As shown in FIG. 5, the lithium ionic liquid obtained in Example 1 was revealed to have a broad potential window.

(3) Charge-Discharge Properties

Preparation of A Coin Cell-Type Secondary Cell

First, a cathode of a coin cell-type secondary battery was prepared. As a binder, PVDF (poly(vinylidene fluoride)) was prepared and dissolved in 1-pyrrolidinone to yield a uniform PVDF solution. Next, LiNi$_{0.8}$Co$_{0.2}$O$_2$ (obtained by heating a mixture of Li$_2$O, NiO and CoO at 720° C. for 24 hours) was prepared as a cathode active material, and acetylene black (AB) was prepared as a conductive material, and these materials were ground and then added gradually to the above PVDF solution. Thereafter, this mixture was stirred vigorously for 24 hours to yield highly viscous slurry. Thereafter, this slurry was applied onto an aluminum substrate prepared as a collector and dried to produce a cathode. The starting materials were prepared such that LiNi$_{0.8}$Co$_{0.2}$O$_2$:PVDF: AB=80:10:10.

Then, an Li metal foil was prepared as an anode of a coin cell-type secondary battery. Thereafter, a coin cell-type secondary battery having a constitution of the cathode/electrolyte-charged Celgard/anode in a glove box filled with argon was prepared.

Method of Evaluating Charge-Discharge Properties

The charge-discharge properties of the coin cell-type secondary battery were evaluated by galvanostatic measurement at a current density of 0.1 mA/cm$^2$ with a battery charging and discharging device (HJ-SM8 system, manufactured by Hokuto Denko Corporation).

Results

Figure 6:
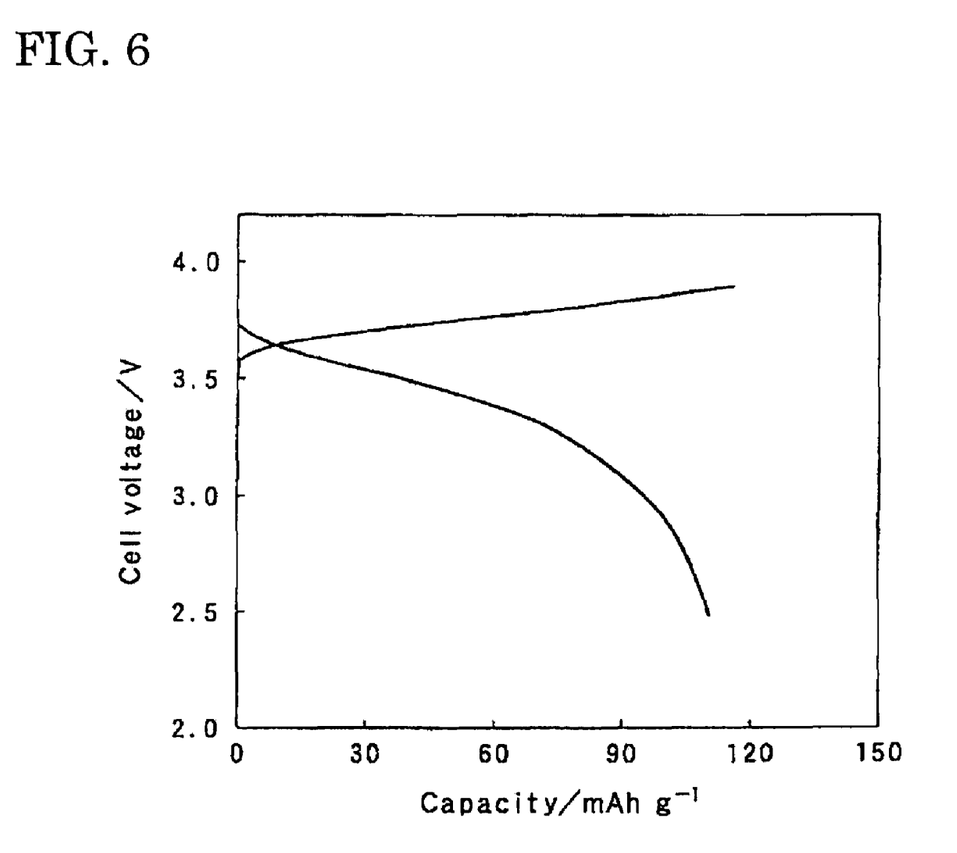
FIG. 6 is a graph showing the charge-discharge properties of a coin-cell type secondary battery using the lithium ionic liquid obtained in Example 1.

FIG. 6 is a graph showing the charge-discharge properties of the coin cell-type secondary battery using the lithium ionic liquid obtained in Example 1. FIG. 6 shows charge-discharge properties in second discharge charge (cutoff voltage: 2.5 to 3.9 V). As shown in FIG. 6, it was revealed that when the lithium ionic liquid obtained in Example 1 was used, a lithium secondary battery having excellent charge-discharge properties could be obtained.

The invention claimed is:

1. A lithium salt comprising a structure represented by the general formula (1):

[Chemical Formula 1]

General Formula (1)

and in the general formula (1), "M" represents B, Si, Ge, P, As or Sb; "X" represents a valence of "M"; "R$_1$" represents —C$_m$H$_{2m}$— in which "m" is an integer of 1 to 4; "R$_2$" represents —C$_k$H$_{2k+1}$ in which "k" is an integer of 1 to 8; and "n" represents 7 to 12.

2. The lithium salt according to claim 1, wherein M$^-$F$_x$ is B$^-$F$_3$ in the general formula (1).

3. The lithium salt according to claim 1, wherein $M^-F_x$ is $B^-F_3$, "$R_1$" is —$C_2H_4$—, and "$R_2$" is —$CH_3$ in the general formula (1).

4. A method for producing a lithium salt, comprising steps of carrying out the following reactions (1) and (2):

[Chemical Formula 2]

$$LiC_pH_{2p+1} + R_2(OR_1)_nOH \rightarrow R_2(OR_1)_nOLi + C_pH_{2p+2}\uparrow \quad \text{(Reaction Formula 1)}$$

$$R_2(OR_1)_nOLi + MF_x \text{Compound} \rightarrow LiMF_xO(R_1O)_nR_2 \quad \text{(Reaction Formula 2)}$$

and in the reaction formulae (1) and (2), "p" represents an integer of 1 to 4; "$R_1$" represents —$C_mH_{2m}$— in which "m" is an integer of 1 to 4; "$R_2$" represents —$C_kH_{2k+1}$ in which "k" is an integer of 1 to 8; "n" represents 0 to 12; "M" represents B, Si, Ge, P, As or Sb; and "X" represents a valence of "M".

5. A lithium salt comprising a structure represented by the general formula (1a):

[Chemical Formula 3]

General Formula (1a)

$$Li^+ \quad \begin{matrix} M^-F_x \\ | \\ O(C_2H_4O)_nCH_3 \end{matrix}$$

and in the general formula (1a), "M" represents B, Si, Ge, P, As or Sb; "X" represents a valence of "M"; and "n" represents 5 to 12.

6. The lithium salt according to claim 5, wherein $M^-F_x$ is $B^-F_3$ in the general formula (1a).

* * * * *

UNITED STATES PATENT AND TRADEMARK OFFICE
CERTIFICATE OF CORRECTION

PATENT NO. : 8,236,980 B2
APPLICATION NO. : 12/377716
DATED : August 7, 2012
INVENTOR(S) : Tatsuo Fujinami et al.

Page 1 of 1

It is certified that error appears in the above-identified patent and that said Letters Patent is hereby corrected as shown below:

Title page, please insert the heading --(30) Foreign Application Priority Data-- and include the following priority information:

--Sept. 13, 2006    (JP)    2006-248539--

Signed and Sealed this
Fifteenth Day of January, 2013

David J. Kappos
*Director of the United States Patent and Trademark Office*